US00PP30627P2

(12) United States Plant Patent
Evans

(10) Patent No.: US PP30,627 P2
(45) Date of Patent: Jul. 2, 2019

(54) ***MALUS* PLANT NAMED 'E756-36'**

(50) Latin Name: *Malus domestica*
Varietal Denomination: E756-36

(71) Applicant: NIAB EMR, Cambridgeshire (GB)

(72) Inventor: Katherine M. Evans, Wenatchee, WA (US)

(73) Assignee: NIAB EMR, Cambridge (GB)

( * ) Notice: Subject to any disclaimer, the term of this patent is extended or adjusted under 35 U.S.C. 154(b) by 0 days.

(21) Appl. No.: 15/732,867

(22) Filed: Jan. 8, 2018

Related U.S. Application Data

(60) Provisional application No. 62/499,452, filed on Jan. 25, 2017.

(51) Int. Cl.
*A01H 5/08* (2018.01)

(52) U.S. Cl.
USPC ..... Plt./161
CPC ..... *A01H 5/08* (2013.01)

(58) Field of Classification Search
USPC ..... Plt./161
See application file for complete search history.

*Primary Examiner* — Anne Marie Grunberg
(74) *Attorney, Agent, or Firm* — Penny J. Aguirre

(57) ABSTRACT

A new cultivar of *Malus* tree, 'E756-36', that is characterized by its fruit with skin that has a red over color with prominent medium sized lenticels, its fruit that is crisp with a pleasant tasting, its fruit that has a medium storage period, and its weak vigor.

3 Drawing Sheets

Botanical classification: *Malus domestica.*
Varietal denomination: 'E756-36'.

BACKGROUND OF THE INVENTION

The present invention relates to a new and distinct cultivar of apple tree, botanically known as *Malus domestica* 'E756-36', referred to hereafter by its cultivar name, 'E756-36'.

'E756-36' arose from an on going breeding program conducted by the Inventor in East Malling, Kent, United Kingdom. The objectives of the breeding program are to develop new cultivars of *Malus* with novel traits with a particular interest in include unique fruit characteristics.

'E756-36' originated as a cross made by the Inventor in 2003 between *Malus domestica* 'Gala' (U.S. Plant Pat. No. 3,637) as the female parent and an unnamed, unpatented proprietary plant in the Inventor's breeding program, reference no. *Malus domestica* 'SA908-12' ('Falstaff', unpatented, x 'Pink Pearl', U.S. Plant Pat. No. 723), as the male parent. The Inventor selected 'E756-36' as a single unique plant amongst the seedlings that resulted from the above cross in 2006.

Asexual propagation of the new cultivar was first accomplished by bud grafting in 2011 under the direction of the Inventor in Italy. Asexual propagation by bud grafting and stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'E756-36' as a unique cultivar *Malus.*

1. 'E756-36' exhibits fruit flesh that is pink in color.
2. 'E756-36' exhibits fruit that has a crisp, juicy and sweet flavor and texture.

3. 'E756-36' exhibits fruit that is useful as a dessert apple (typically pink fleshed apples are more tart).
4. 'E756-36' exhibits fruit that can be used in fresh market and processing.

The female parent of 'E756-36', 'Gala', is similar to 'E756-36' in having a moderately vigorous growth habit and fruit that can be used in desserts. 'Gala', differs from 'E756-36' in having fruit flesh that is white to yellow in color. The male parent, 'SA908-12', is similar to 'E756-36' in having fruit flesh that is pink in color. 'SA908-12' differs from 'E756-36' in having fruit with a less sweet and more tart flavor. 'E756-36' can also be compared to the cultivars 'Pink Pearl' (U.S. Plant Pat. No. 723) and 'Howell TC2' (U.S. Plant Pat. No. 28,545). 'Pink Pearl' is similar to 'E756-36' in having fruit flesh that is pink in color. 'Pink Pearl' differs from 'E756-36' in having fruit that is conical in shape, fruit that has a tarter flavor and fruit skin color that is red with an orange flush. 'Howell TC2' is similar to 'E756-36' in having distinctive fruit and fruit flesh coloration. 'Howell TC2' differs from 'E756-36' in having fruit flesh that is dark pink and red in color and fruit that has a tart flavor.

BRIEF DESCRIPTION OF THE DRAWINGS

The accompanying colored photographs illustrates the overall appearance and distinct characteristics of the new apple tree. The photograph was taken of fruit on a 2 year-old plant of 'E756-36' as grown outdoors in the ground in East Malling, Kent, United Kingdom.

The photograph in FIG. 1 provides a view of a tree in fruit of 'E756-36'.

Figure 1:
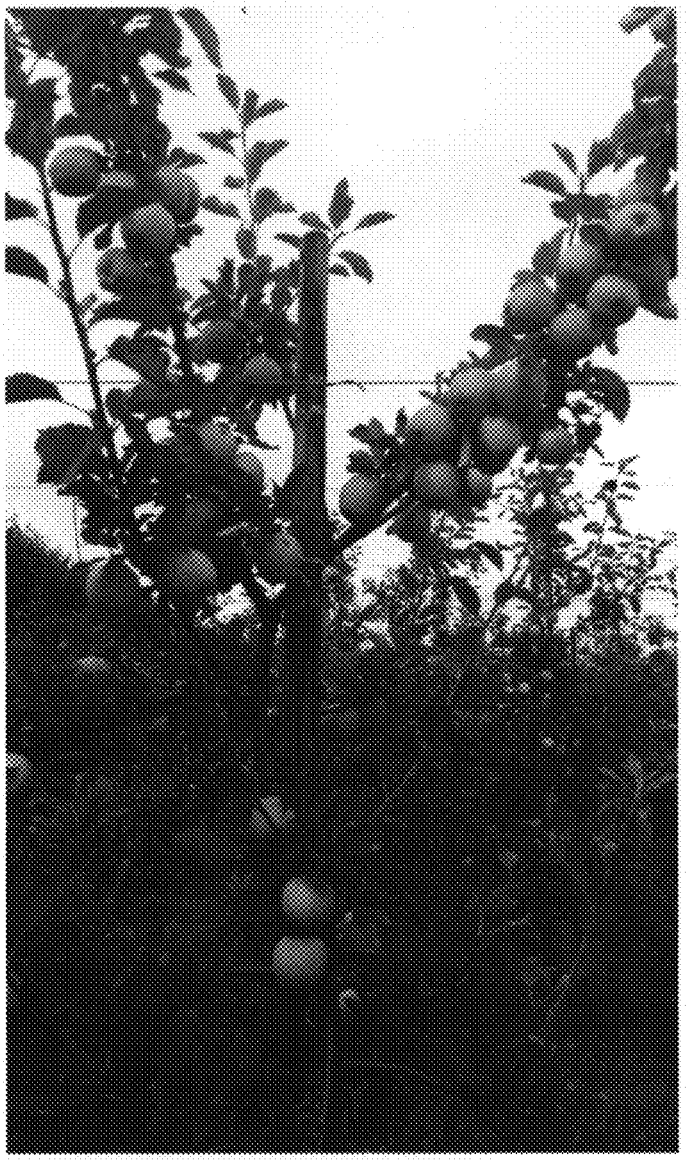
Figure 2:
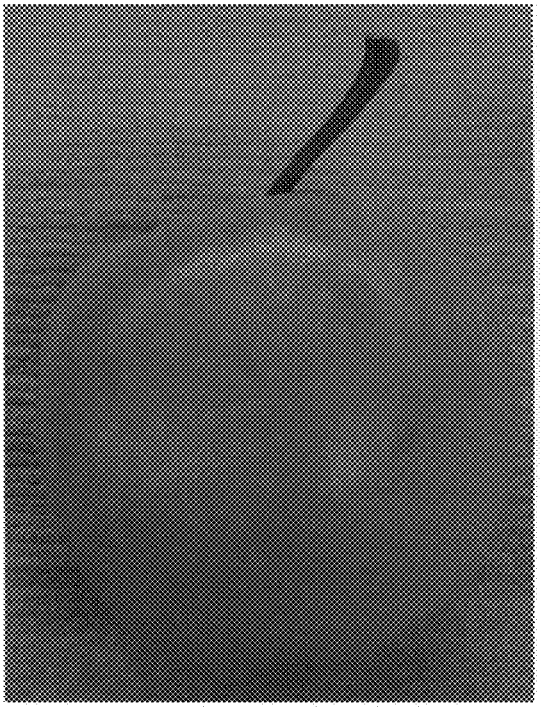

The photograph in FIG. 2 provides a close-up view of a fruit the 'E756-36'.

Figure 3:
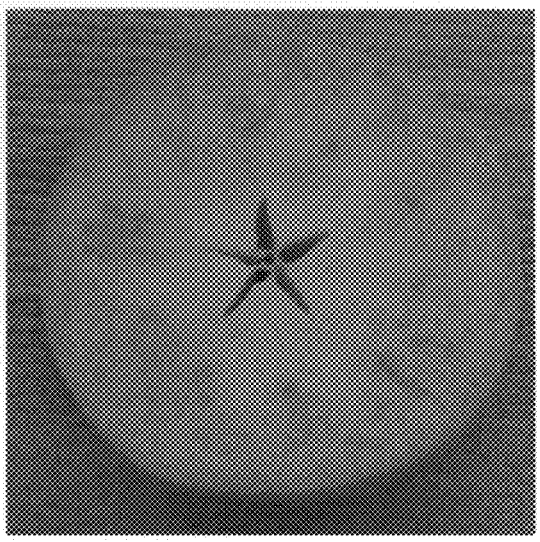

The photograph in FIG. 3 provides a close-up view of the fruit flesh of 'E756-36'.

Figure 4:
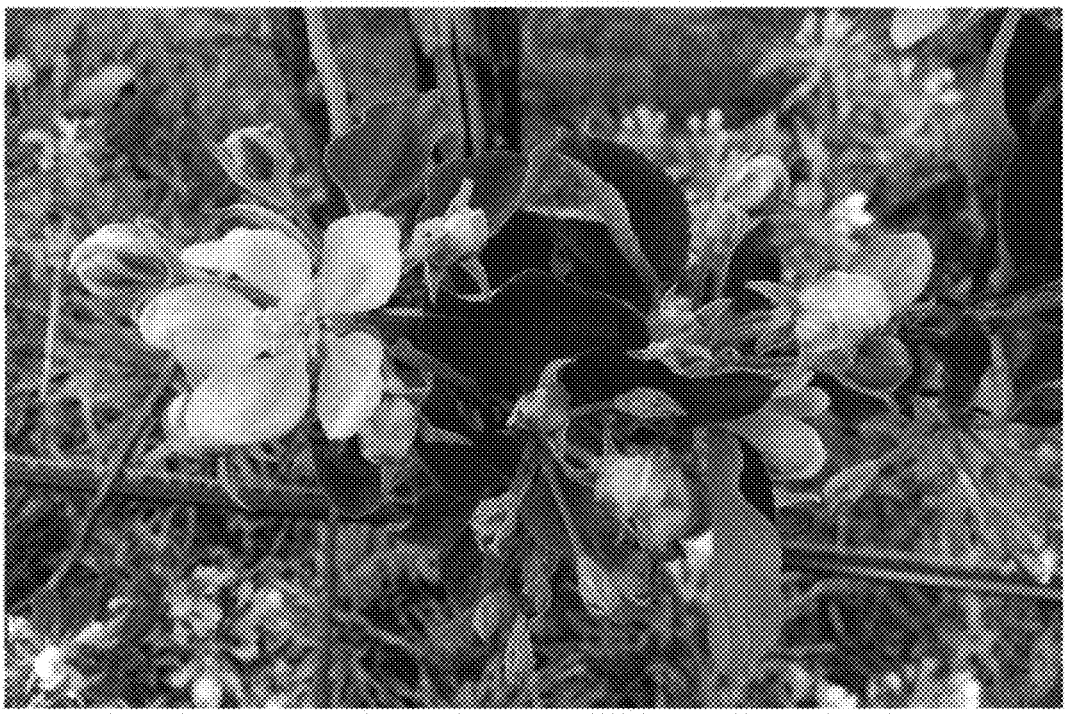

The photograph in FIG. 4 provides a close-up view of the flowers of 'E756-36'.

Figure 5:
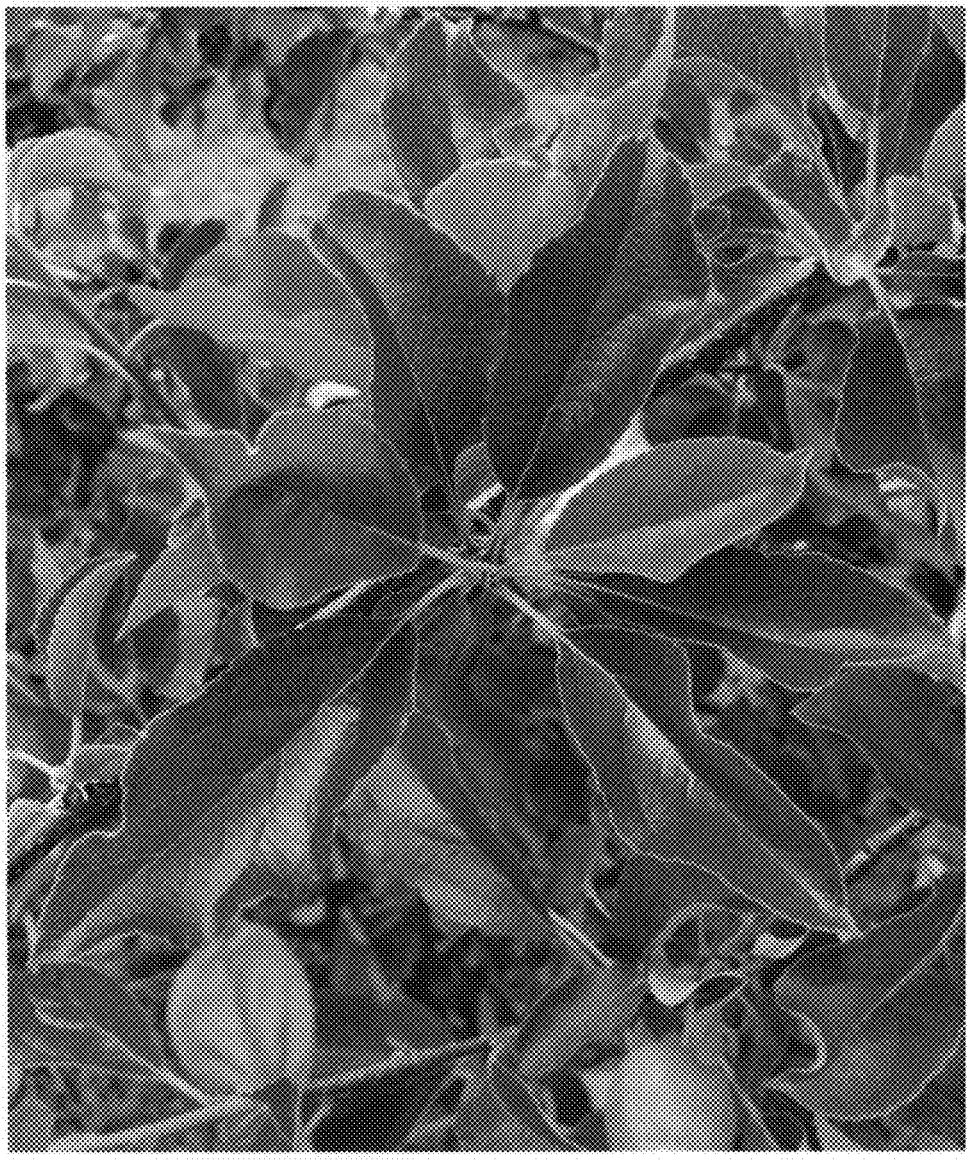

The photograph in FIG. 5 provides a close-up view of the foliage of 'E756-36'.

The colors in the photographs are as close as possible with the photographic and printing technology utilized and the color values cited in the detailed botanical description accurately describe the colors of the new *Malus*.

DETAILED BOTANICAL DESCRIPTION

The following is a detailed description of the new apple variety as observed on two year-old plants as grown outdoors in the ground in East Malling, Kent, United Kingdom. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

Tree description:

*Plant type*.—Deciduous fruiting tree.

*Plant habit*.—Ramified, upright.

*Height and spread*.—An average of 2.55 m in height and 1.42 m in width.

*Cold hardiness*.—At least to U.S.D.A. Zone 8.

*Disease and pest resistance/susceptibility*.—None noted.

*Propagation*.—Vegetative budding, grafting and stem.

*Growth rate*.—Moderately vigorous.

Description of branches:

*Frequency*.—Medium.

*Angle*.—Upright

*Bearing*.—Predominantly spur-bearing, some bearing on tips.

*Bark color*.—201C, with underlying 177A.

Description of one year-old shoots:

*Pubescence on upper one year-old shoot*.—Weak.

*Shine of bark*.—Moderate.

*Flexibility*.—Medium to strong.

*Thickness of shoot at center of middle internode*.—Average of 6.6 mm.

*Bark color*.—201C, with underlying 177A.

*Shoot angle*.—Approximately 60°.

*Lenticels*.—Prominent, circular in shape, 8.45 mm in length and diameter, 101 per sq. cm, 155C in color.

Description of growing shoots:

*Color of growing tip of shoot*.—139D.

*Shape of shoot tips leaves in cross section*.—Slightly carinate.

*Pubescence of shoot tip leaves*.—Moderate on lower leaf surface.

*Color of shoot tip leaves*.—Both surfaces 144A.

*Distribution of color other than green on shoot tips leaves*.—151A, outer margins 175A.

Leaf description:

*Leaf orientation*.—Upward.

*Leaf arrangement*.—Alternate.

*Leaf division*.—Simple.

*Leaf shape*.—Elliptic.

*Leaf quantity*.—Average of 219 per lateral branch

*Leaf size*.—New shoot leaf; average of 8.5 cm in length, 4.6 cm in width, fruit spur leaf; 5.7 cm in length, 3.1 cm in width.

*Leaf apex*.—Mucronate to cuspidate.

*Leaf base*.—Rounded to slightly oblique.

*Leaf surface*.—Upper surface; glossy, lower surface; glabrous.

*Leaf margin*.—Crenulate to serrulate.

*Leaf color*.—Young; upper surface 144A, lower surface 146C, mature; upper surface 141A, lower surface 146C.

*Leaf anthocyanin on upper surface*.—Present on base of petioles and veins.

*Leaf venation*.—Pinnate, upper surface between 180B and 160D in color, lower surface 160D in color.

*Petiole size*.—Average of 2.2 cm in length.

*Petiole color*.—Upper surface 144D, 181A at base, lower surface 145C.

*Stipules*.—Average of 7.8 mm in length, 141A in color.

Flower description:

*Blooming period*.—April in East Mailing, Kent, United Kingdom.

*Number of flowers*.—Average of 5 per spur.

*Inflorescence type*.—Corymb of rotate flowers.

*Flower buds*.—Average of 1.7 cm in length, 0.7 cm in diameter, the bud color at balloon stage is dark pink (186B) at the base with a lighter shade of pink on the tip (186D), elliptic with an obtuse tip in shape.

*Flower size*.—Up to 3.5 cm in diameter and 3.6 cm in depth.

*Flower fragrance*.—Mild.

*Flower aspect*.—Upright.

*Petals*.—5 per flower, un-fused, sometimes overlapping, ovate in shape, round apex, round base, entire margin, up to 2.5 cm in length and 1.3 cm in width, color; when opening upper and lower surface a blend of 155A and 186B, when fully open upper surface 155A, slightly tinged with 186B, when fully open lower surface 186B, upper and lower surface silky, glabrous.

*Sepals*.—5 per flower, slight to moderately covered with villous hairs on both surfaces, linear in shape, entire margin, acute apex, intercalate, average of 9.5 mm in length and 4 mm in width, young and mature upper and lower surface color 194A.

*Calyx*.—Inverted cone shape, 8.8 mm in height, 4.5 mm in diameter.

*Pedicel*.—Average of 2 cm in length and 1.2 mm in width, glabrous surface, 194A in color.

*Pistil*.—Compound carpel with 5 stigmas fused at base, style and stigma together measure 6 mm in length, color is 160B, turning into 162A as they mature, the ovary is inferior and the stigmas are just below the height of the anthers.

*Stamens*.—Average of 20, anther; basifixed in shape, 160B in color and 2.5 mm in length, 1.5 mm in width, pollen; none observe.

Fruit description:

*Fruit size*.—Medium, 6.52 cm in diameter, average of 6.73 cm in height.

*Position of maximum diameter*.—Two fifths of the length from the proximal to the distal end.

*Fruit shape*.—Conic.

*Fruit symmetry*.—Slightly asymmetric.

*Fruit prominence of ribbing*.—Weak.

*Fruit aperture of eye*.—Open, eye basin: Deep and broad, an average of 2.42 cm in depth and 5.4 mm in width.

*Persistence of calyx*.—Persistent.

*Length of sepal*.—Average of 1.06 cm.

*Spacing of sepals at base*.—2.44 mm.

*Stalk*.—Thin to medium thickness, an average of 2.2 mm thick and 2.6 cm in length.

*Depth of stalk cavity*.—Broad and medium depth, an average of 1.04 cm in depth, and 3.1 cm in width.

*Relief of surface*.—Smooth.

*Skin*.—Non-waxy, texture; thin, and smooth.

*Skin color*.—Ground color of skin: orange yellow (168B), over-color of skin: pink orange (179B), pattern of over-color: blush with some mottling.

*Presence of russet*.—Around stalk basin toward the eye basin, 5% of apples heavily russeted.

*Lenticels*.—1.18 mm in diameter, prominent, greyed-orange (163D).

*Color of flesh*.—A blend of 180D and 179B, core 161D.

*Distinctness of core line*.—Low.

*Aperture of locules*.—Fully open.

*Fruit maturity date*.—Approximate harvest date is first week of September in East Mailing, Kent, United Kingdom.

*Browning of flesh*.—High resistance.

*Texture of flesh*.—Crisp and juicy.

*Cropping frequency*.—Annual cropping.

*Acidity*.—3.4 pH, titratable acid 0.71±0.02 g malic acid/100 ml.

*Brix*.—An average of 14.2%.

*Seed*.—Average of 5 per fruit, ranges in groups 166 and 200, ovoid to somewhat deltoid in shape, an average of 9 mm in length and 5.5 mm in width and 2.8 mm in thickness.

*Storage life*.—3 to 4 months in common storage (average temperature of 34° F.).

It is claimed:

1. A new and distinct variety of *Malus* tree named 'E756-36' as herein illustrated and described.

* * * * *